(12) United States Patent
Yoshioka et al.

(10) Patent No.: US 9,823,228 B2
(45) Date of Patent: Nov. 21, 2017

(54) CHROMATOGRAPH MASS SPECTROMETER AND CONTROL METHOD THEREFOR

(71) Applicant: HITACHI HIGH-TECHNOLOGIES CORPORATION, Tokyo (JP)

(72) Inventors: Shinji Yoshioka, Tokyo (JP); Hiromichi Yamashita, Tokyo (JP); Akira Maekawa, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 15/312,792

(22) PCT Filed: Jul. 29, 2015

(86) PCT No.: PCT/IB2015/001277
§ 371 (c)(1),
(2) Date: Nov. 21, 2016

(87) PCT Pub. No.: WO2015/189696
PCT Pub. Date: Dec. 17, 2015

(65) Prior Publication Data
US 2017/0097328 A1  Apr. 6, 2017

(51) Int. Cl.
*G01N 30/86* (2006.01)
*G01N 30/72* (2006.01)
(52) U.S. Cl.
CPC ......... *G01N 30/8658* (2013.01); *G01N 30/72* (2013.01); *G01N 30/8631* (2013.01)

(58) Field of Classification Search
USPC ....... 250/281, 282, 283, 286, 287, 288, 299, 250/526; 436/161, 173
See application file for complete search history.

(56) References Cited

U.S. PATENT DOCUMENTS 5,015,848 A * 5/1991 Bomse .................. G01M 3/202
250/281
5,600,134 A * 2/1997 Ashe .................. G01N 33/2829
250/252.1

(Continued)

FOREIGN PATENT DOCUMENTS

JP 60-253963 A 12/1985
JP 04-294271 A 10/1992

(Continued)

OTHER PUBLICATIONS

International Search Report, dated Oct. 13, 2015, which issued during the prosecution of International Application No. PCT/IB2015/001277 which corresponds to the present application.

*Primary Examiner* — Bernard Souw
(74) *Attorney, Agent, or Firm* — Baker Botts L.L.P.

(57) ABSTRACT

A technician is forced to determine the measurement time to be used in a selected ion monitoring (SIM) measurement while observing mass spectral data. Thus, mass spectral data and one or a plurality of mass chromatogram data items is generated on the basis of the detection results of an ion detection unit, and, for each corresponding ion component, the measurement time to be used in SIM is determined on the basis of the elution time range represented by each peak waveform of the one or plurality of mass chromatogram data items that have been generated.

10 Claims, 8 Drawing Sheets

(56) References Cited

U.S. PATENT DOCUMENTS

| | | | |
|---|---|---|---|
| 7,161,141 B2* | 1/2007 | Mimura | H01J 49/0009 250/252.1 |
| 7,202,471 B2* | 4/2007 | Hondo | G01N 30/7233 210/656 |
| 2005/0253060 A1* | 11/2005 | Mimura | H01J 49/0009 250/281 |
| 2006/0145070 A1* | 7/2006 | Hondo | G01N 30/7233 250/288 |
| 2006/0255258 A1* | 11/2006 | Wang | G01N 30/8624 250/282 |
| 2008/0110232 A1 | 5/2008 | Miyagawa | |

FOREIGN PATENT DOCUMENTS

| | | |
|---|---|---|
| JP | 09-229920 A | 9/1997 |
| JP | 2006-010323 A | 1/2006 |
| JP | 2010-032277 A | 2/2010 |

\* cited by examiner

CHROMATOGRAPH MASS SPECTROMETER AND CONTROL METHOD THEREFOR

CROSS REFERENCE TO PRIOR APPLICATIONS

This application is a U.S. National Phase application under 35 U.S.C. §371 of International Application No. PCT/IB2015/001277, filed on Jul. 29, 2015, which claims benefit of priority to Japanese Application No. 2014-121043, filed on Jun. 12, 2014. The International Application was published in Japanese on Dec. 17, 2015 as WO 2015/189696 A1 under PCT Article 21(2). The contents of the above applications are hereby incorporated by reference.

TECHNICAL FIELD

The present invention relates to a chromatograph mass spectrometer and a method of controlling the same.

BACKGROUND ART

In recent years, a quantitative analysis method using a liquid chromatograph mass spectrometer has been used for chemical components and metabolite in biological samples and residues in environmental samples, and the like in many cases. A mass spectrometer is used as a high-sensitivity detector for liquid chromatography. Examples of the mass spectrometer include a quadrupole mass spectrometer, an ion trapping mass spectrometer, and a time-of-flight mass spectrometer, and these mass spectrometers are used depending on purposes of measurement. For quantitative analysis, the quadrupole mass spectrometer is used in many cases.

The quadrupole mass spectrometer can measure a mass number by two schemes, namely scanning measurement and selected ion monitoring (SIM). In the scanning measurement, scanning is performed within a predetermined mass number range, and spectra of ions included in the set mass number range are detected. This scanning method is used for qualitative analysis of unknown samples, for example. In the SIM measurement, chromatograms of ions with specific mass numbers designated in advance are selectively detected. This method is used in a case where analysis target components are known and quantitative analysis of the components is performed with high sensitivity.

In the related art, it is necessary for a technician to scan and measure a target sample in advance, to check mass spectra of detected components, and to determine mass numbers as targets of the SIM measurement in a case of determining the mass numbers for the SIM measurement. Thereafter, the mass numbers selected by the technician are used to display the mass chromatograms, and a characteristic mass number is determined for each target peak of the SIM measurement.

However, there is no means for automatically selecting an optimal mass number (maximum intensity or the like) for each peak in the liquid chromatograph mass spectrometer in the related art. Therefore, the spectrometer selects the mass number for each peak based on the determination by the technician, then extracts a mass chromatogram corresponding to the selected mass number, and further determines elution time (start and end time of the chromatogram) of the extracted mass chromatogram. In a case where the number of components as targets of measurement is large, it is necessary to set time for performing optimal SIM measurement in consideration of overlapping of the respective component peaks and the like, and there is a problem that it takes long time for the technician to determine and execute SIM measurement conditions.

According to Patent Literature 1, a mass number corresponding to each targeted component of quantitative analysis is determined by scanning data of the component as quantitative analysis in advance and is regarded as a mass number at the time of the SIM measurement. Patent Literature 1 is characterized in that mass spectrometry of the mass number corresponding to each targeted component is performed for predetermined time before and after a peak timing regardless of differences in the targeted components.

CITATION LIST

Patent Literature 1: JP-A-2006-010323

SUMMARY OF INVENTION

However, according to the method of setting the SIM measurement time within predetermined time before and after the peak timing (that is, a fixed time length), it is necessary for the technician to visually check chromatogram data and to set measurement time for each component in a case where elution time of the components separated by the liquid chromatography differs. Therefore, it takes time to determine SIM measurement conditions. According to the method described in Patent Literature 1, it is not possible to automatically set an elution time range suitable for each peak even if there is variations in elution time ranges of the components separated by the liquid chromatography.

Thus, the invention provides a chromatograph mass spectrometer that determines measurement time used for SIM measurement for each target component in consideration of base line information determined from a shape of an actual chromatogram peak.

In order to solve the above problem, a configuration described in claims, for example, is employed. The specification includes a plurality of means for solving the above problem, and one example thereof is characterized in that "mass spectral data and one or a plurality of mass chromatogram data items are generated based on a result of detection by an ion detection unit, and measurement time used for selected ion monitoring is determined for each corresponding ion component based on an elution time range appearing in each peak waveform of the generated one or a plurality of mass chromatogram data items.

The specification includes content of disclosure in Japanese Patent Application No. 2014-121043 as a basis of the right of priority of the present application.

Advantageous Effects of Invention

According to the invention, it is possible to determine optimal measurement time for each peak waveform without visually checking mass spectral data. Problems, configurations, and advantages other than those described above will be clarified by the following description of an embodiment.

DESCRIPTION OF EMBODIMENTS

Hereinafter, description will be given of an embodiment of the invention with reference to drawings. Embodiments of the invention are not limited to the example described below, and various modifications can be made within a scope of the technical idea.

[Apparatus Configuration]

Figure 1:
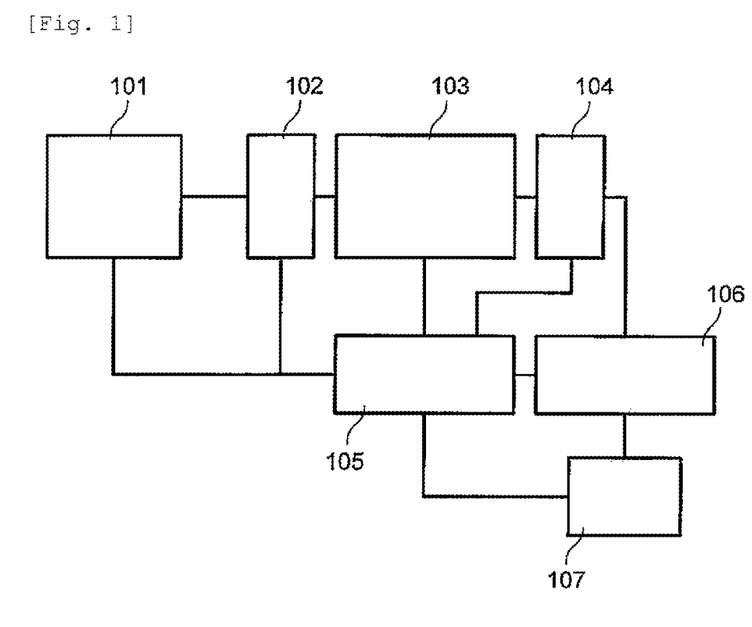
FIG. 1 is a diagram illustrating an outline configuration of a liquid chromatography mass spectrometer.

FIG. 1 illustrates an outline configuration of a liquid chromatography mass spectrometer. Many samples analyzed by the liquid chromatograph mass spectrometer are samples in which a plurality of components are present together. Thus, samples are purified by preprocessing or the like in accordance with the respective samples and are then separated by an LC (liquid chromatograph) unit 101. The samples after the separation are introduced into an ion source 102 of the mass spectrometer and is ionized. The ion source 102 as an ion generation unit uses an electrospray ionization method (ESI) or an atmospheric pressure chemical ionization method (APCI) that is typically used in a liquid chromatograph mass spectrometer.

The components ionized by the ion source 102 are introduced from the atmospheric pressure into the vacuum, and is then subjected to mass separation by an MS (mass spectrometry) unit 103 with a quadrupole mass spectrometer. In the embodiment, a quadrupole mass spectrometer is used as the MS (mass spectrometry) unit 103. Otherwise, the MS unit 103 may be a triple-quadrupole mass spectrometer with a collision cell. The quadrupole mass spectrometer can measure mass numbers by two schemes, namely scanning measurement and selected ion monitoring (SIM). In the scanning measurement, scanning is performed within a predetermined mass number range, and ions included in the set mass number range are detected. This scanning method is used for qualitative analysis of unknown samples, for example. In the SIM measurement, only ions with specific mass numbers designated in advance are selectively detected. This method is used in a case where analysis target components are known and quantitative analysis of the components is performed with high sensitivity. The ions after being subjected to the mass separation by the MS (mass spectrometry) unit 103 are sequentially detected by an ion detection unit 104 arranged in a later stage.

Operations of the LC (liquid chromatograph) unit 101, the ion source 102, the MS (mass spectrometry) unit 103, and the ion detection unit 104 are controlled by a control unit 105. Control conditions are set by the control unit 105 through an input unit 107. A signal ion-detected by the ion detection unit 104 is output to a data processing unit 106. The data processing unit 106 executes accumulation, storage, analysis, and the like of data information and outputs the data after the analysis and the like. An instruction for performing the analysis operation and the like of the data processing unit 106 is provided from the input unit 107.

Here, the MS (mass spectrometry) unit 103 successively obtains data as a basis of a mass spectrum in accordance with scanning conditions set by the input unit 107 in synchronization with a start of the separation of the sample components by the LC (liquid chromatograph) unit 101. The data processing unit 106 accumulates the data of the mass spectrum indicating a relationship of ion intensity with respect to a mass charge ratio for every observed holding time.

[Setting and Determination of SIM Conditions]

Figure 2:
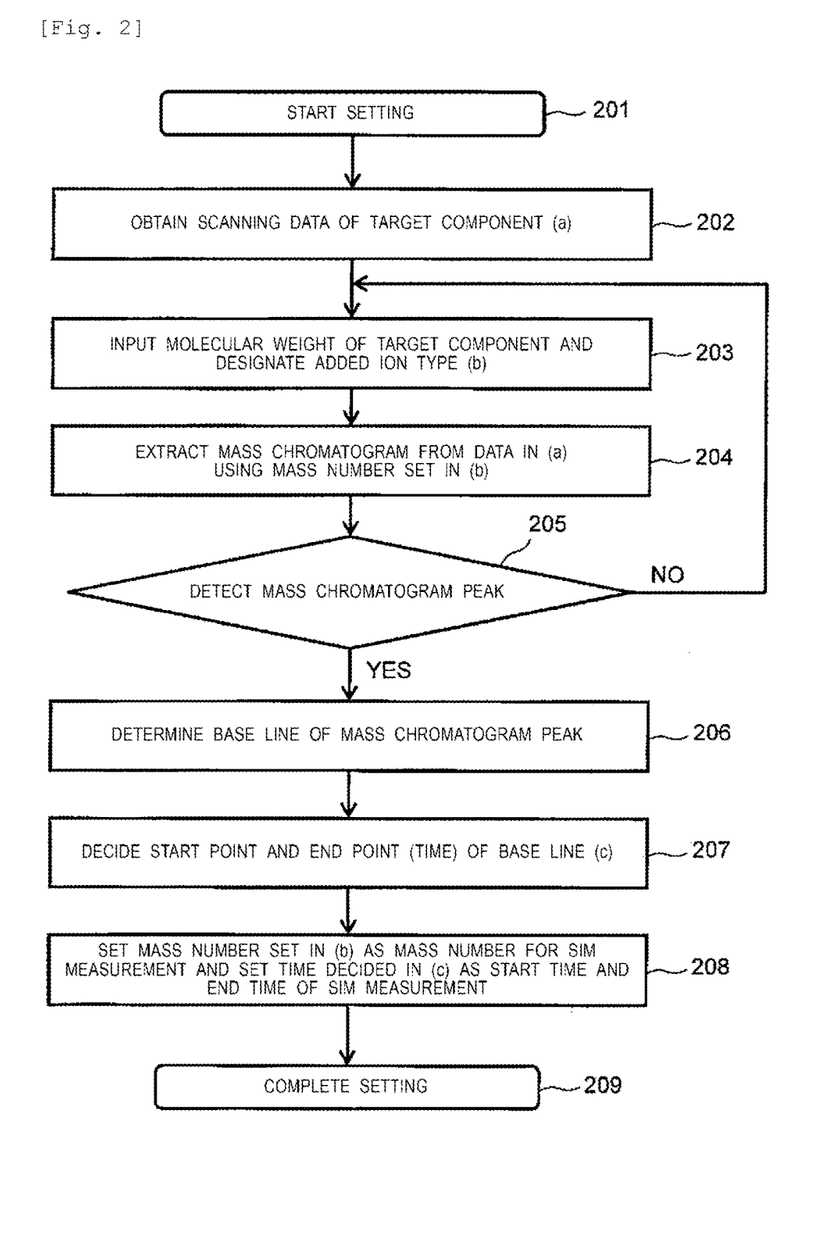
FIG. 2 is a flowchart illustrating a flow of SIM measurement condition determination processing.

FIG. 2 illustrates a flow of processing of determining and deciding SIM conditions proposed in the embodiment. The respective steps illustrated in FIG. 2 are executed in accordance with a program that is stored in advance in storage devices of the control unit 105 and the data processing unit 106. The processing illustrated in FIG. 2 proceeds in an order of (1) designation of a mass number of an ion peak corresponding to a component as a target of SIM measurement from scanning data, (2) extraction of a mass chromatogram of the corresponding mass number, (3) determination of a peak of the extracted chromatogram, (4) determination of a base line of the detected peak, (5) determination of a peak selection width, and (6) reflection to SIM measurement conditions.

First, the control unit 105 starts processing of setting SIM measurement conditions (Step 201) and obtains scanning data including a target component (Step 202). At this time, the control unit 105 controls the MS (mass spectrometry) unit 103 using a quadrupole mass spectrometer based on the conditions set in advance by the input unit 107, and performs scanning measurement. As for separation conditions of the LC (liquid chromatograph) unit 101, the measurement is performed under the same conditions as separation conditions employed when quantitative analysis is performed by actually using SIM scanning. In a case where the scanning data has already been obtained before the setting is performed, it is also possible to select the obtained scanning data and use the scanning data for the analysis in the following flowchart.

Figure 3:
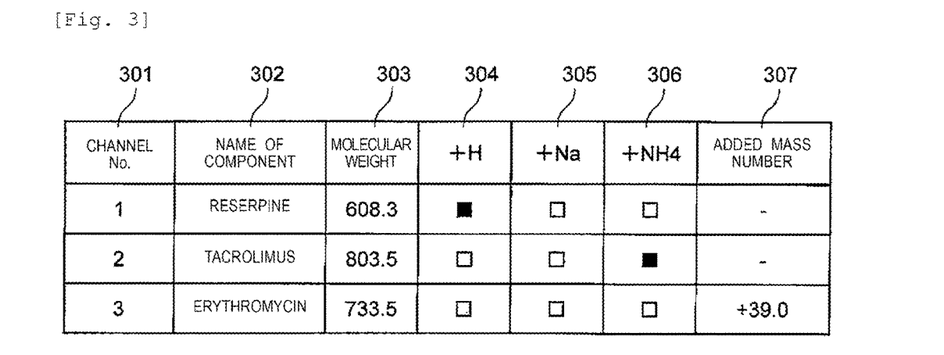
FIG. 3 is a diagram illustrating an example of a condition input screen when a molecular ion as a target component is searched.

Next, conditions for ion-extracting each component from data of a target sample after the scanning measurement are input to the control unit 105 through the input unit 107 (condition setting screen) (Step 203). FIG. 3 illustrates a configuration example of the condition setting screen. A setting item 301 corresponds to a channel for performing the SIM measurement and is a number of components when quantitative analysis is actually performed. In a case of performing SIM measurement on three components, three settings are needed as the "channel No.". A name of a component that is actually subjected to the quantitative analysis is input to a setting item 302. The name of the component may be manually input by the technician or may be selected from names of components prepared in advance. A molecular weight corresponding to the component in the setting item 302 is set in a setting item 303. As the molecular weight, an unavailable ion pattern of a molecular ion when the ion is actually generated by the electrospray ionization method (ESI) or the atmospheric pressure chemical ionization method (APCI) is designated. An item 304 is a section for designating and inputting a proton-added ion, an item 305 is a section for designating and inputting a sodium-added ion, and an item 306 is a section for designating and inputting an ammonium-added ion. An item 307 is a section for designating and inputting an ion type that does not correspond to the items 304 to 306 and is used for setting an added mass number for designating the ion type. The technician can arbitrarily set an added mass number in the item 307.

In a case where the technician designates a proton-added ion in the item 304 (checks the check box), the control unit 105 adds "+1.0" to a mass number which has already been input to a corresponding channel. In a case where the technician designates a sodium-added ion in the item 305 (checks the check box), the control unit 105 adds "+23.0" to the mass number which has already been input to the corresponding channel. In a case where the technician designates an ammonium-added ion in the item 306 (checks the check box), the control unit 105 adds "+18.0" to the mass number which has already been input to the corresponding channel. In a case where the technician inputs an arbitrary mass number in the item 307, the control unit 105 adds an added mass number to the mass number which has already been input to the corresponding channel, and regards the result as a mass number condition used for extracting a mass chromatogram. That is, the control unit 105 sets the mass number of the molecular ion calculated in accordance with the setting on a condition setting screen (FIG. 3) as a mass number condition for extracting a mass chromatogram.

Although FIG. 3 illustrates an example in which one added ion is selected for each channel, a plurality of added ions can be selected. In the case where a plurality of added ions are selected for one channel, the control unit 105 selects chromatogram data with the maximum peak intensity in the plurality of mass chromatogram data items in the following step 205 and performs the following processing. This processing makes it possible to search for mass number information with which the maximum signal intensity can be obtained even in a case in which detection of a plurality of ion peaks is assumed.

In the example in FIG. 3, mass number information of "channel No. 1" is 609.3 (=608.3+1.0), mass number information of "channel No. 2" is 821.5 (=803.5+18.0), and mass number information of "channel No. 3" is 772.5 (=733.5+39.0) depending on the content input to the condition setting screen. The control unit 105 may have a function of changing a molecular weight and precision in an added ion mass used for the calculation depending on precision of the mass spectrometer.

Figure 4:
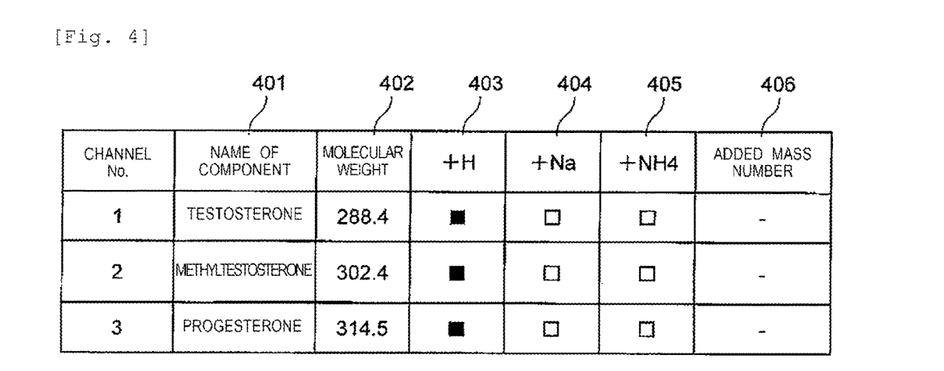
FIG. 4 is a diagram illustrating an example of a condition input screen when molecular ions of three components are searched.

FIG. 4 illustrates an example of a condition input screen used for searching for molecular ions of three components. In this embodiment, an example of an SIM condition setting screen when quantitative analysis is performed on three components, namely testosterone, methyltestosterone, and progesterone is shown. Testosterone, methyltestosterone, and progesterone are input as names of components as the item 401. A molecular weight of 288.4 is input for testosterone, a molecular weight of 302.4 is input for methyltestosterone, and a molecular weight of 314.5 is input for progesterone as the item 402. In the case of FIG. 4, only the proton-added ion in the item 403 is designated as a molecular ion to be extracted in the three components. Therefore, mass number information obtained by adding +1.0 to the molecular weight numerical value instead of the information in the items 404 to 406 is used as the molecular ion mass number when the mass chromatogram of each component is extracted from the scanning data.

In the following Step 204, the control unit 105 extracts mass chromatograms from actual scanning data in accordance with the setting conditions (mass number information of the molecular ion corresponding to each channel) received in Step 203. In the case of FIG. 4, the control unit 105 extracts 289.4 (=288.4+1.0) for testosterone, 303.4 (=302.4+1.0), for methyltestosterone, and 315.5 (=314.5+1.0), for progesterone as molecular ion mass numbers.

In actual extraction processing, it is also possible to cause the mass numbers calculated in Step 203 to have a width before and after the mass numbers. For example, a selected width designated in the program in advance is used as a selected width for extracting mass chromatograms. A scheme of determining the selected width based on mass precision of the mass spectrometer used is employed. In the embodiment, a selected width of ±0.2 is used. In this case, mass chromatograms are extracted within the range of ±0.2 with respect to the mass numbers of the molecular ions of the respective components calculated in Step 203. Therefore, a mass chromatogram with a mass width from 289.2 to 289.6 is extracted for the "channel No. 1". Also, a mass chromatogram with a mass width from 303.2 to 303.6 is extracted for the "channel No. 2".

Also, a mass chromatogram with a mass width from 315.3 to 315.7 is extracted for the "channel No. 3".

Figure 5:
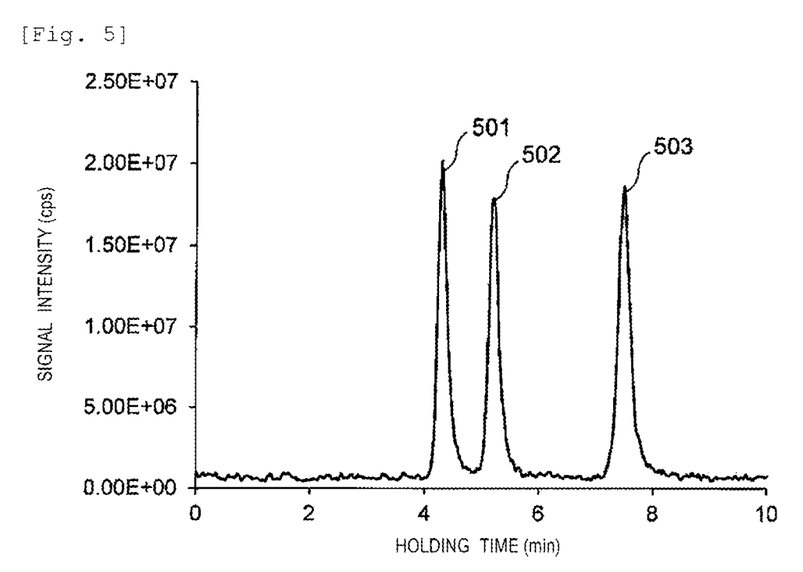
FIG. 5 is a diagram illustrating total ion chromatograms of the three components.

FIG. 5 illustrates an example of total ion chromatogram data obtained by scanning and measuring the three components, namely testosterone, methyltestosterone, and progesterone by the liquid chromatography mass spectrometer illustrated in FIG. 1. As illustrated in FIG. 5, peak waveforms of the three components are detected in the mass chromatogram. In practice, a peak waveform 501 corresponds to a peak of testosterone, a peak waveform 502 corresponds to a peak of methyltestosteron, and a peak waveform 503 corresponds to a peak of progesterone in an order from the peak of early elution time. As described above, the control unit 105 extracts the mass chromatogram using the mass number information of the molecular ions in Step 203 from the scanning data illustrated in FIG. 5.

Figure 6:
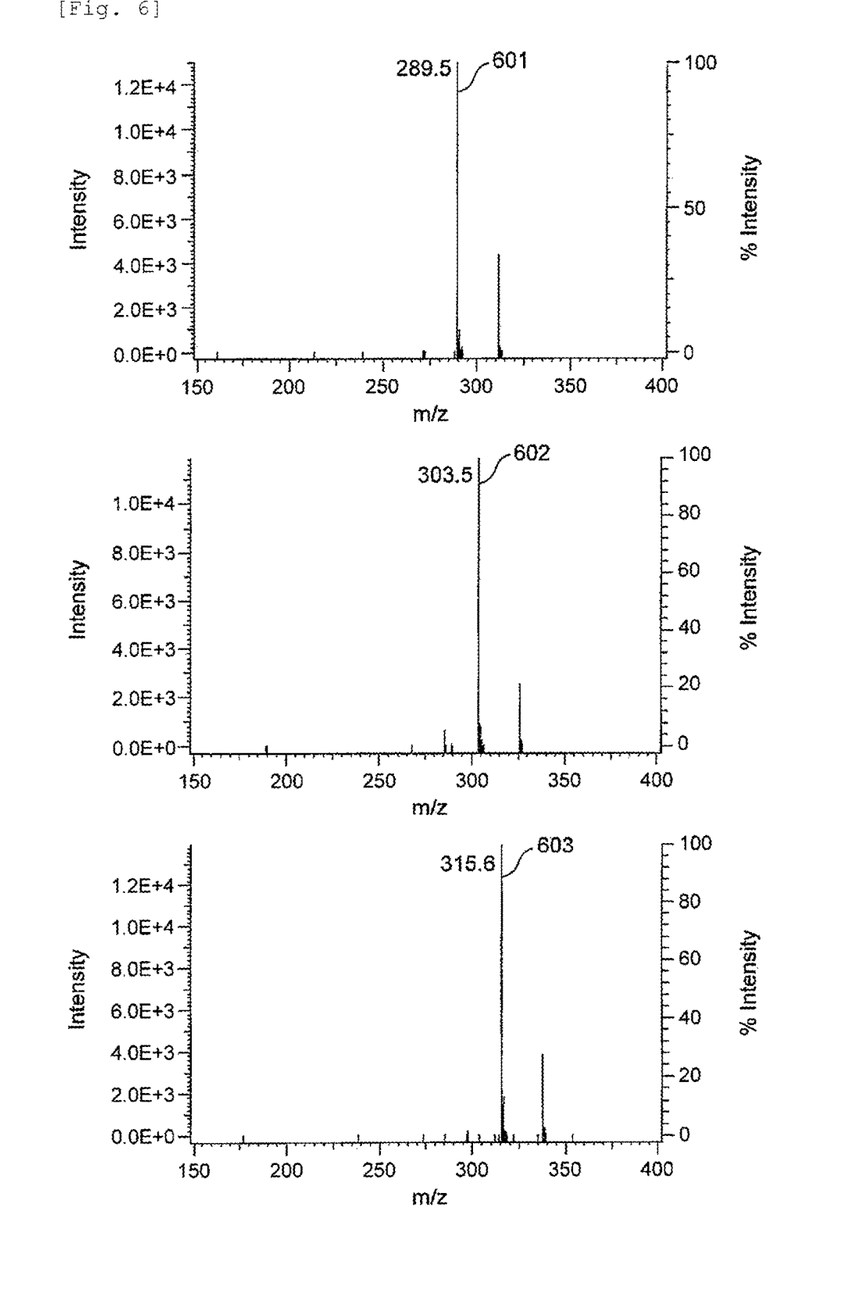
FIG. 6 is a diagram illustrating mass spectra of the three components.

FIG. 6 is a diagram illustrating mass spectral data of the three components from the scanning data in FIG. 5.

FIG. 6 illustrates mass spectral data of testosterone, methyltestosterone, and progesterone in a direction from the highest stage to the lowest stage. In the drawing, a peak 601 corresponds to the mass number 289.5 and coincides with the range of the mass number 289.4 of the proton-added ion of testosterone, which is calculated in Step 203, ±0.2. Similarly, a peak 602 corresponds to the mass number of 303.5 and coincides with the range of the mass number 303.4 of the proton-added ion of the methytestosterone, which is calculated in Step 203, ±0.2. Similarly, a peak 603 corresponds to the mass number 315.6 and coincides with the range of the mass number 315.5 of the proton-added ion of progesterone, which is calculated in Step 203, ±0.2. In the embodiment, it is possible to selectively extract the mass chromatogram peaks of the respective components by designating the proton-added ions.

Figure 7:
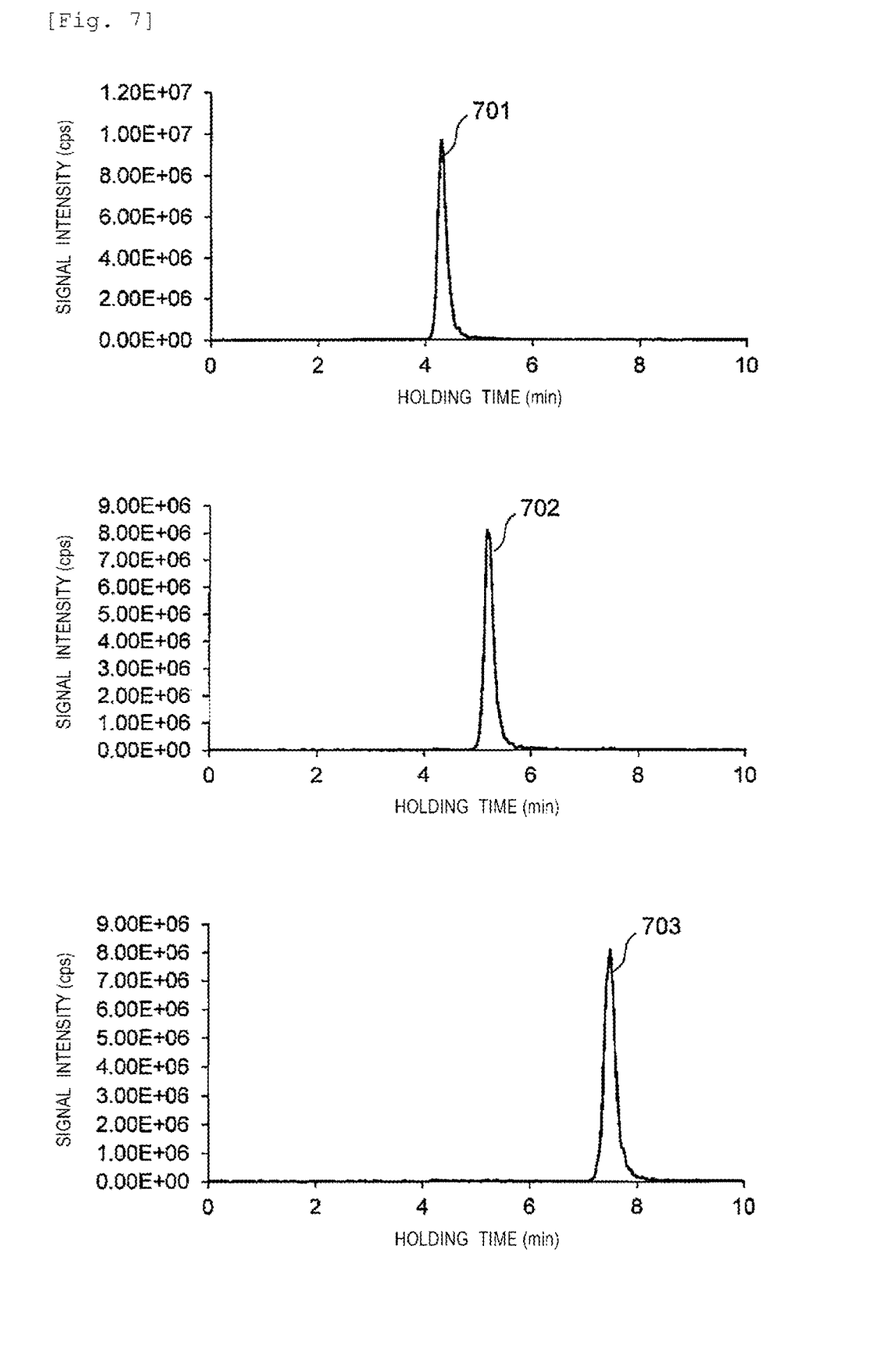
FIG. 7 is a diagram illustrating mass chromatograms of the three components.

FIG. 7 is a diagram illustrating mass chromatogram data of the three components when the extraction is performed in Step 204. FIG. 7 illustrates mass chromatogram data of testosterone 701, methyltestosterone 702, and progesterone 703 in a direction from the highest stage to the lowest stage. FIG. 7 illustrates a result of performing extraction by using the mass number information of the molecular ions calculated in Step 203 and the mass width of ±0.2. Although both the start time and the end time are extended with the same time range in this example, the start time and the end time may be extended with different time ranges.

In the following Step 205, the control unit 105 performs peak determination of the mass chromatogram data of the respective components extracted in Step 204. In the peak determination, the control unit 105 performs the peak determination by using a threshold value determined for signal intensity, for example. It is desirable that threshold value conditions of signal intensity can be changed by the technician in accordance with noise intensity or the like of data.

After the extraction of the mass chromatograms, the control unit 105 determines that a peak has been detected in a case where a peak with signal intensity detected to be higher than a preset threshold value is detected. In a case where a peak with signal intensity that is lower than the threshold value is detected, the control unit 105 returns to Step 203 and executes the processing in Step 204 and the following steps again on the other added ion types.

Figure 8:
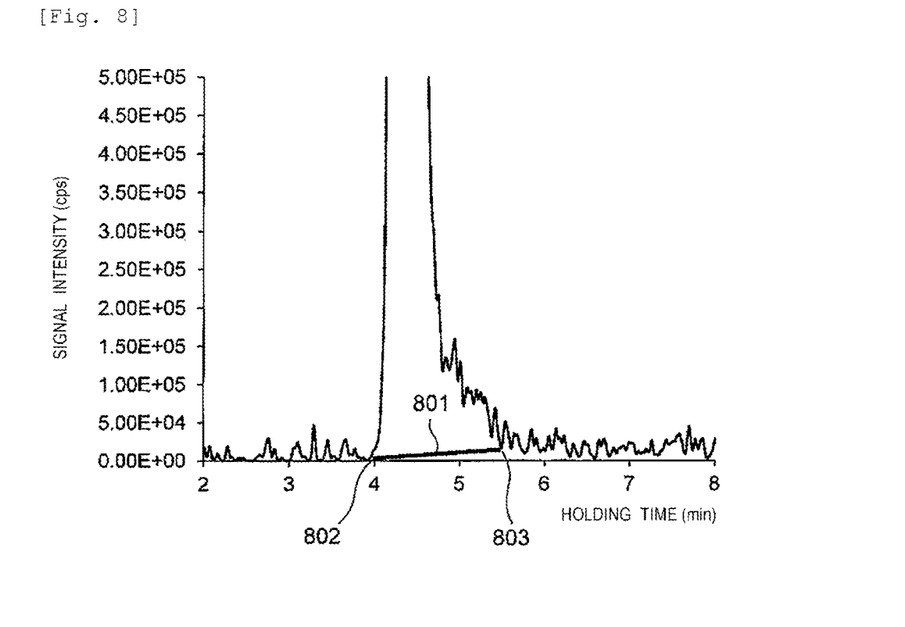
FIG. 8 is a diagram illustrating an example in which a base line of a mass chromatogram is determined.

In relation to the chromatogram peaks detected in Step 205, the control unit 105 performs base line determination in Step 206. FIG. 8 illustrates an example of data of the base line determination performed on the mass chromatogram peak of testosterone. Since various methods have already been proposed as methods of determining the base line 801, detailed description will be omitted. The base line 801 is determined as a straight line connecting a start point 802 and an end point 803 of the peak waveform detected in the process of determination. In the processing of determining the base line, for example, an apex of the peak waveform is detected first, and the start point 802 and the end point 803 of the peak are then detected in order.

In the next Step 207, the control unit 105 obtains time information of the start point 802 and the end point 803 of the peak from the information of the base line 801. The time information is basic information for determining a measurement time range when the SIM measurement of the corresponding component is performed. As described above, the base line 801 is determined for each peak waveform, and the measurement time range (the start time and the end time) is individually and automatically determined based on the information according to the embodiment. Therefore, it is possible to greatly reduce burden required for an operation of setting the measurement time suitable for each peak waveform even in a case where the technician is not familiar with the operation of the liquid chromatography mass spectrometer.

Although the start time and the end time of the base line 801 obtained in Step 207 may be set as start time and end time for performing the SIM measurement of a corresponding channel number without any change, it is also possible to use a combination with a measurement time automatic extending function. In a case where an extended time range (0.1 minutes, for example) is set in advance in the program, for example, the control unit 105 may automatically extend the measurement time, set timing obtained by adding −0.1 minutes to the start time 802 of the base line 801 as new start time, and set timing obtained by adding +0.1 minutes to the end time 803 as new end time. The presence of this automatic extending function can prevent the measurement time range from lacking from an originally necessary time range even in a case where the elution time range of the chromatogram peak changes depending on concentration (in a case where a peak shape changes due to so-called tailing or the like). A relationship between a measurement peak waveform and optimal measurement time in a case of measuring the same samples with different concentrations will be described later.

In Step 208, the control unit 105 registers, as SIM measurement condition information of each component, the time information (the start time 802 and the end time 803) determined in Step 207 by the mass number information of the molecular ions calculated in Step 203. After the registration processing, the control unit 105 completes the processing of setting the SIM measurement conditions (Step 209).

[Example of Display Screen for Setting Result]

Figure 9:
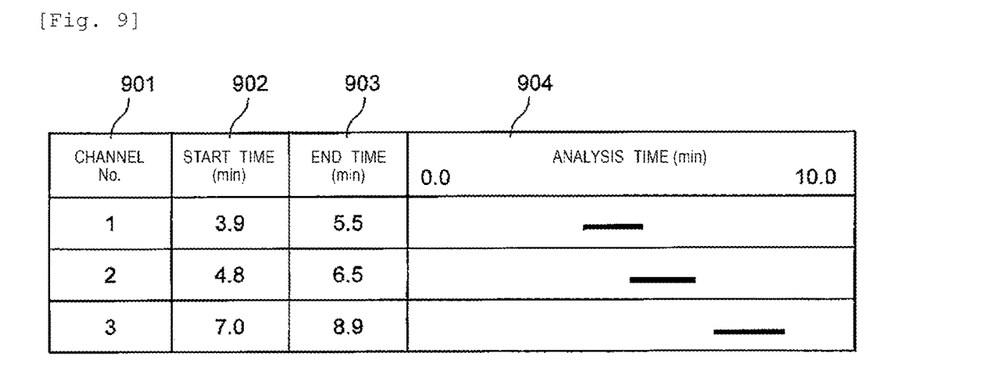
FIG. 9 is a diagram illustrating an example of a display screen for content of determination of SIM conditions.

FIG. 9 illustrates an example of a screen displayed as an interface screen after the completion of the processing of setting the SIM measurement conditions. It is a matter of course that the information on the display screen is generated based on the SIM condition information of each component set and registered in Step 208. In the drawing, an item 901 is a channel number, an item 902 is start time of the SIM measurement, an item 903 is end time of the SIM measurement, and an item 904 is arrangement of the measurement time of each channel in the entire analysis time. In the case of FIG. 9, the measurement time of testosterone (SIM measurement mass number: 289.5) continues for 1.6 minutes from 3.9 minutes to 5.5 minutes, the measurement time of methyltestosterone (SIM measurement mass number: 303.5) continues for 1.7 minutes from 4.8 minutes to 6.5 minutes, and the measurement time of progesterone (SIM measurement mass number: 315.6) continues for 1.9 minutes from 7.0 minutes to 8.9 minutes. In the drawing, the measurement time of each component is represented by a horizontal bar on the time axis.

[Relationship Between Differences in Sample Concentration and Optimal Measurement Time]

Figure 10:
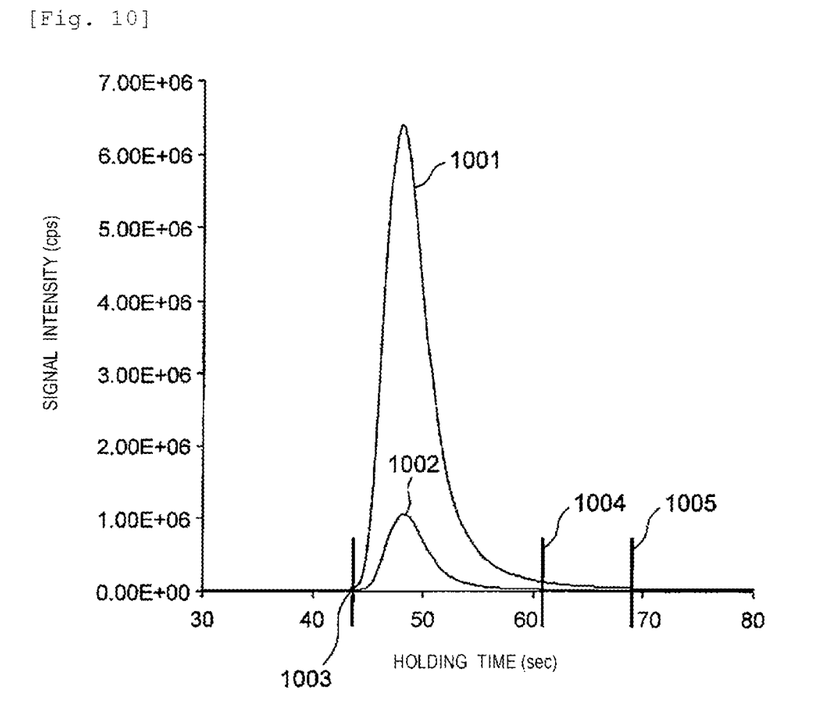
FIG. 10 is an explanatory diagram of a relationship between mass chromatograms of samples with differences in concentration and optimal measurement time ranges.

FIG. 10 illustrates a relationship between measurement peak waveforms and optimal measurement time in a case of measuring the same samples with differences in concentration. In the drawing, both peak waveforms 1001 and 1002 are chromatograms measured for samples containing the same components. In the case illustrated in the drawing, the sample corresponding to the peak waveform 1001 corresponds to higher concentration than that of the sample corresponding to the peak waveform 1002.

In comparison between the base lines of the peak waveform 1001 of the high-concentration sample and the peak waveform 1002 of the low-concentration sample, the start points 1003 are substantially the same. However, the end point 1004 of the peak waveform 1002 of the low-concentration sample is about 61 seconds while the end point 1005 of the peak waveform of the high-concentration sample is about 69 seconds, and a delay of about 8 seconds from the endpoint 1004 is observed. As described above, there is a possibility that the end points of the measured peak waveforms differ from each other if concentrations of the same sample differ from each other. This means that the measurement time range determined when the SIM measurement of the low-concentration sample is performed cannot be used for the SIM measurement of the high-concentration sample without any change. If the measurement time for the SIM measurement determined for the low-concentration sample is applied to the measurement time for the SIM measurement of the high-concentration sample without any change, the measurement time ends in the process of elution of the high-concentration sample as illustrated in FIG. 10. That is, the measurement time (or the measurement time range) for the low-concentration sample is not an optimal value as the measurement time (or the measurement time range) for the high-concentration sample. As a result, a possibility that the result of the SIM measurement performed on the high-concentration sample does not exhibit a correct value increases.

Thus, the base line 801 is determined and the measurement time (or the measurement time range) is determined for each measurement sample, and start timing and end timing of the measurement time (or the measurement time range) for the SIM measurement determined for a specific concentration are respectively extended in the aforementioned embodiment. Although the measurement time is extended by constant time in both the directions before and after the measurement time in the above description, it is also possible to provide a setting function capable of extending the measurement time only for the start time or the end time. In a case where the start time of the base lines is substantially the same regardless of the difference in sample concentrations as illustrated in FIG. 10, for example, it is possible to perform accurate measurement regardless of the difference in sample concentrations by preparing a function of extending the end time of the measurement time.

That is, if the measurement time (or the measurement time range) for the SIM measurement on a sample with a specific concentration (a low-concentration sample, for example) is determined, the control unit 105 sets extension time of +10 seconds for the determined end time of the SIM measurement. In a case where the control unit 105 automatically sets the SIM measurement time to 71 seconds obtained by adding 10 seconds to 61 seconds as the end time determined for the low-concentration sample as described above, it is possible to perform the SIM measurement over the entire elution time range of the high-concentration sample since the end point 1005 (69 seconds) of the base line of the high-concentration sample is included in the automatically set measurement time.

The extending time can be commonly provided for the respective components, or can be separately provided for the respective components as described above. Although the technical advantage of the embodiment was described in which it was possible to accurately perform the SIM measurement regardless of variations in the measurement time (or the measurement time range) between the same samples with different concentrations, the measurement time (or the measurement time range) extending function is also effective for variations in peak shapes due to degradation of a separation column used in the liquid chromatograph.

Advantages of the Embodiment

As described above, it is possible to automatically determine a mass number and measurement time (or measurement time range) when SIM measurement of each component designated as a measurement target is performed by using corresponding scanning data as long as the liquid chromatography mass spectrometer according to the embodiment is used. Therefore, it is possible not only to eliminate necessity for a technician to visually check mass spectral data but also to greatly reduce operation burden for setting the measurement time (measurement time range) in accordance with a molecular ion type as the measurement target.

According to the liquid chromatography mass spectrometer of the embodiment, the measurement time (or the measurement time range) of each component is determined based on information of a base line individually determined for each peak waveform as described above. Therefore, it is possible to easily determine optimal SIM measurement time (or the measurement time range) for each component even in a case where an elution time range is different for each component. Also, time required for obtaining a result of the SIM measurement may be reduced by using the aforementioned measurement time extending function and applying time (or a time range) obtained by extending the SIM measurement time (or the measurement time range) determined for a sample after measurement in a case where a measurement target is the same sample with a different concentration.

Other Embodiments

The invention is not limited to the configuration of the aforementioned embodiment and includes various modifications. Although the description was given of the application to the liquid chromatography mass spectrometer in the aforementioned embodiment, for example, an application may be made to a gas chromatography mass spectrometer. Although the detection of the mass chromatogram, the determination of the base line, and the like are executed to determine the measurement time for each component after the acquisition of the scanning data of the target component is completed (after Step 202 is competed) in the aforementioned embodiment, the measurement time for the peak waveform corresponding to each component may be determined in a simultaneous parallel manner (in real time) with the operation of detecting the scanning data of the target component. It is possible to further reduce the time required for setting the SIM measurement conditions by using the function.

A part of embodiments was described in detail for clearly describing the invention, and all the configurations described above in the aforementioned embodiment may not necessarily be provided. It is also possible to add other configurations to the configurations of the aforementioned embodiment, to replace the configurations of the aforementioned embodiment with other configurations, or to delete a part of the configurations of the embodiment.

A part or an entirety of the functions of the control unit 105 in the aforementioned embodiment may be realized by an integrated circuit or other hardware, for example. Information such as a program, a table, and a file used for realizing the functions of the control unit 105 can be stored in a storage device such as a memory, a hard disk, or an SSD (Solid State Drive) or a storage medium such as an IC card, an SD card, or a DVD.

Not all control lines and information lines necessary as a product but only control lines and information lines that were considered to be necessary for the description were illustrated. It may be considered that substantially all the configurations are connected to each other in practice.

REFERENCE SIGNS LIST

101: LC (liquid chromatograph) unit
102: ion source
103: MS (mass spectrometry) unit
104: ion detection unit
105: control unit
106: data processing unit
107: input unit All publications, patents, patent applications cited in this specification are incorporated herein for references.

The invention claimed is:
1. A chromatograph mass spectrometer comprising:
a chromatograph unit that separates a sample;

an ion source unit that ionizes components separated by the chromatograph unit;

a mass spectrometry unit that separates the components ionized by the ion source unit depending on masses;

an ion detection unit that detects ion components after mass separation;

a data processing unit that generates mass spectral data and one or a plurality of mass chromatogram data items; and a control unit that determines measurement time used for selected ion monitoring for each corresponding ion component based on start time and end time of each peak determined by a base line of each peak waveform of the one or a plurality of mass chromatogram data items.

2. The chromatograph mass spectrometer according to claim 1, wherein the control unit sets, as the measurement time, time obtained by adding time with a predetermined width before and/or after a time range corresponding to the base line.

3. The chromatograph mass spectrometer according to claim 1, wherein the control unit determines each peak waveform of the one or a plurality of mass chromatogram data items in parallel with an operation of detecting scanning data by the ion detection unit, and then determines the measurement time for each ion component.

4. The chromatograph mass spectrometer according to claim 1, wherein the chromatograph unit is a liquid chromatograph.

5. The chromatograph mass spectrometer according to claim 1, wherein the chromatograph unit is a gas chromatograph.

6. A method of controlling a chromatograph mass spectrometer including a chromatograph unit that separates a sample, an ion source unit that ionizes components separated by the chromatograph unit, a mass spectrometry unit that separates the components ionized by the ion source unit depending on masses, an ion detection unit that detects ion components after mass separation, a data processing unit that generates mass spectral data and one or a plurality of mass chromatogram data items based on a result of the detection by the ion detection unit, and a control unit that controls operations of the mass spectrometry unit and the ion detection unit, the method comprising:

causing the control unit to determine measurement time used for selected ion monitoring for each corresponding ion component based on start time and end time of each peak determined by a base line of each peak waveform of the one or a plurality of mass chromatogram data items.

7. The method of controlling a chromatograph mass spectrometer according to claim 6, wherein the control unit sets, as the measurement time, time obtained by adding time with a predetermined range before and/or after a time range corresponding to the base line.

8. The method of controlling a chromatograph mass spectrometer according to claim 6, wherein the control unit determines each peak waveform of the one or a plurality of mass chromatogram data items in parallel with an operation of detecting scanned data by the ion detection unit, and then determines the measurement time for each ion component.

9. The method of controlling a chromatograph mass spectrometer according to claim 6, wherein the chromatograph unit is a liquid chromatograph.

10. The method of controlling a chromatograph mass spectrometer according to claim 6, wherein the chromatograph unit is a gas chromatograph.

* * * * *